United States Patent
Yamazaki et al.

(10) Patent No.: US 9,796,963 B2
(45) Date of Patent: Oct. 24, 2017

(54) GLUCOSE DEHYDROGENASE

(71) Applicant: TOYOBO CO., LTD., Osaka-shi, Osaka (JP)

(72) Inventors: Yasuhiro Yamazaki, Tsuruga (JP); Yosuke Sumida, Tsuruga (JP); Rie Hirao, Tsuruga (JP); Yuu Utashima, Tsuruga (JP); Hiroshi Aiba, Tsuruga (JP); Takahide Kishimoto, Tsuruga (JP); Shusaku Yanagidani, Tsuruga (JP)

(73) Assignee: Toyobo Co., Ltd., Osaka (JP)

( * ) Notice: Subject to any disclaimer, the term of this patent is extended or adjusted under 35 U.S.C. 154(b) by 4 days.

(21) Appl. No.: 14/426,679

(22) PCT Filed: Sep. 6, 2013

(86) PCT No.: PCT/JP2013/074067
§ 371 (c)(1),
(2) Date: Mar. 6, 2015

(87) PCT Pub. No.: WO2014/038660
PCT Pub. Date: Mar. 13, 2014

(65) Prior Publication Data
US 2015/0240216 A1     Aug. 27, 2015

(30) Foreign Application Priority Data

Sep. 10, 2012 (JP) .................. 2012-198498

(51) Int. Cl.
*C12N 9/00* (2006.01)
*C12Q 1/54* (2006.01)
*C12N 9/04* (2006.01)

(52) U.S. Cl.
CPC ............ *C12N 9/0006* (2013.01); *C12Q 1/54* (2013.01)

(58) Field of Classification Search
None
See application file for complete search history.

(56) References Cited

U.S. PATENT DOCUMENTS

| | | |
|---|---|---|
| 2006/0063217 A1 | 3/2006 | Omura et al. |
| 2008/0003628 A1* | 1/2008 | Kitabayashi ......... C12N 9/0006 435/14 |
| 2008/0220460 A1 | 9/2008 | Kawaminami et al. |
| 2009/0176262 A1 | 7/2009 | Omura et al. |
| 2009/0317848 A1 | 12/2009 | Kawaminami et al. |
| 2010/0297743 A1 | 11/2010 | Omura et al. |
| 2011/0318810 A1 | 12/2011 | Tajima et al. |
| 2012/0122130 A1 | 5/2012 | Omura et al. |
| 2012/0246255 A1 | 9/2012 | Walker et al. |
| 2013/0309750 A1 | 11/2013 | Tajima et al. |
| 2014/0057331 A1 | 2/2014 | Tajima et al. |
| 2014/0154777 A1 | 6/2014 | Sumida et al. |
| 2014/0234533 A1 | 8/2014 | Omura et al. |
| 2015/0024461 A1 | 1/2015 | Nishio et al. |

FOREIGN PATENT DOCUMENTS

| | | |
|---|---|---|
| JP | 2007-289148 A | 11/2007 |
| JP | 2008-237210 A | 10/2008 |
| JP | 2013-090621 A | 5/2013 |
| WO | WO 2004/058958 A1 | 7/2004 |
| WO | WO 2006/101239 A1 | 9/2006 |
| WO | WO 2008/059777 A1 | 5/2008 |
| WO | WO 2010/140431 A1 | 12/2010 |
| WO | WO 2011/068050 A1 | 6/2011 |
| WO | WO 2012/073986 A1 | 6/2012 |
| WO | WO 2012/073987 A1 | 6/2012 |
| WO | WO 2013/022074 A1 * | 2/2013 |

OTHER PUBLICATIONS

Tang et al., "Design of Freeze-Drying Processes for Pharmaceuticals: Practical Advice", Pharmaceutical Research, vol. 21, No. 2, Feb. 2004, pp. 191-200.*
Japan Patent Office, International Search Report in International Patent Application No. PCT/JP2013/074067 (Nov. 12, 2013).
Griebenow et al., "Lyophilization-induced reversible changes in the secondary structure of proteins," *Proc. Natl. Acad. Sci.*, 92: 10969-10976 (1995).

* cited by examiner

*Primary Examiner* — Suzanne M Noakes
(74) *Attorney, Agent, or Firm* — Leydig, Voit & Mayer, Ltd.

(57) ABSTRACT

The present invention provides a novel glucose dehydrogenase that has excellent substrate specificity and that is suitable for use in SMBG. The present invention provides a flavin-bound glucose dehydrogenase having the following characteristics (1) to (5): (1) Temperature stability: stable at a temperature of 45° C. or lower; (2) stable at a pH range of 4.5 to 7.5; (3) substrate specificity: the reactivity to D-xylose, maltose, or D-galactose is 2% or less, based on the reactivity to D-glucose taken as 100%; (4) optimal activity temperature: 34 to 47° C.; and (5) optimal activity pH: 6.3 to 6.7.

8 Claims, 3 Drawing Sheets

GLUCOSE DEHYDROGENASE

CROSS-REFERENCE TO RELATED APPLICATIONS

This patent application is the U.S. national phase of International Patent Application No. PCT/JP2012/074067, filed Sep. 6, 2013, which claims the benefit of Japanese Patent Application No. 2012-198498, filed on Sep. 10, 2012, which are incorporated by reference in their entireties herein.

TECHNICAL FIELD

The present invention relates to a glucose dehydrogenase (hereinafter also referred to as "GDH"). More specifically, the present invention relates to a flavin-bound glucose dehydrogenase (hereinafter also referred to as "FGDH"), a fungus that produces the flavin-bound glucose dehydrogenase, a method for producing the flavin-bound glucose dehydrogenase, a method for measuring glucose using the flavin-bound glucose dehydrogenase, and the like.

BACKGROUND ART

Self-monitoring of blood glucose (SMBG) is important for diabetic patients to manage their blood glucose levels and to use this monitoring in treatment. Simple blood glucose self-monitoring devices using an electrochemical biosensor have recently found wide use in SMBG. The biosensor includes an insulating substrate on which electrodes and an enzyme reaction layer are formed.

Examples of enzymes used herein include glucose dehydrogenase (GDH), glucose oxidase (GO), and the like. In terms of methods using GO (EC 1.1.3.4), a problem has been noted in that dissolved oxygen in a measurement sample is likely to affect the measurement results. Although GDH is unaffected by dissolved oxygen, it is not suitable for accurately measuring blood glucose levels, because, for example, a pyrroloquinoline quinone-dependent glucose dehydrogenase (PQQ-GDH) (EC 1.1.5.2 (formerly EC 1.1.99.17)) acts on sugars such as maltose and lactose, in addition to glucose.

A flavin adenine dinucleotide-dependent glucose dehydrogenase (hereinafter also referred to as "FADGDH") is known as a flavin-bound glucose dehydrogenase that is unaffected by dissolved oxygen and that has almost no action on maltose. For example, Patent Documents 1 to 5 report enzymes derived from *Aspergillus terreus* and *Aspergillus oryzae*, and modifications of these. These enzymes, however, have relatively high reactivity to xylose (Patent Document 1), and there is therefore room for improvement in accurately measuring the blood glucose of people who are undergoing a xylose tolerance test. Meanwhile, a flavin-bound GDH having relatively low action on xylose (Patent Document 6), a modified GDH having combined advantages of GO and GDH (Patent Document 7), and the like, have been developed, but there is still room for improvement.

PRIOR ART REFERENCE

Patent Documents

Patent Document 1: WO2004/058958
Patent Document 2: WO2006/101239
Patent Document 3: JP2007-289148A
Patent Document 4: JP2008-237210A
Patent Document 5: WO2008/059777
Patent Document 6: WO2010/140431
Patent Document 7: WO2011/068050

SUMMARY OF INVENTION

Technical Problem

Under the above circumstances, the present inventors conducted intensive research to develop a novel glucose dehydrogenase that is more suitable for use in SMBG, and found that the use of an enzyme having high substrate specificity and excellent stability enables the measurement time to be shortened while accurately measuring blood glucose levels with a small amount of enzyme. More specifically, an object of the present invention is to provide a novel glucose dehydrogenase that has excellent substrate specificity, thermal stability, and the like, and is thus suitable for use in SMBG sensors.

Solution to Problem

The present inventors conducted intensive research to achieve the above object. As a result of screening many microorganisms, they found that some microorganisms that had not been reported to produce glucose dehydrogenase have glucose dehydrogenase activity. The inventors then isolated and purified this enzyme, analyzed its characteristics, and thereby found that this enzyme was a flavin-bound glucose dehydrogenase that has excellent substrate specificity.

The present invention has been accomplished as a result of further research and improvement based on these findings. Representative examples of the present invention are described below.

Item 1. A flavin-bound glucose dehydrogenase having the following characteristics (1) to (5):
(1) Temperature stability: stable at a temperature of 45° C. or lower;
(2) Stable at a pH range of 4.5 to 7.6;
(3) Substrate specificity: the reactivity to D-xylose, maltose, or D-galactose is 2% or less, based on the reactivity to D-glucose taken as 100%;
(4) Optimal activity temperature: 43 to 47° C.; and
(5) Optimal activity pH: 6.3 to 6.7.

Item 2. The flavin-bound glucose dehydrogenase according to Item 1, further having the following characteristic (6):
(6) Derived from microorganisms of the genus *Arthrinium* and the genus *Apiospora*, which is the sexual stage of *Arthrinium*.

Item 3. A method for producing the flavin-bound glucose dehydrogenase of Item 1 or 2, the method comprising:

culturing a microorganism of the genus *Arthrinium* or the genus *Apiospora*, which is the sexual stage of *Arthrinium*; and collecting a glucose dehydrogenase.

Item 4. A method for measuring glucose concentration, the method comprising causing the flavin-bound glucose dehydrogenase of Item 1 or 2 to act on glucose.

Item 5. A glucose assay kit comprising the flavin-bound glucose dehydrogenase of Item 1 or 2.

Item 6. A glucose sensor comprising the flavin-bound glucose dehydrogenase of Item 1 or 2.

Advantageous Effects of Invention

The flavin-bound glucose dehydrogenase (FGDH) of the present invention has significantly reduced reactivity to maltose, D-galactose, or D-xylose; therefore, even when D-glucose and these sugars are present together in a sample, the amount and the concentration of glucose can be accurately measured. Further, the FGDH of the present invention is stable within a wide pH range, and thus it can be suitably used under a wide range of conditions. With these characteristics, the FGDH of the present invention makes it possible to accurately measure the glucose concentration in any sample containing D-glucose (e.g., blood and food (such as seasonings and beverages)).

DESCRIPTION OF EMBODIMENTS

The present invention is described below in detail.
1. Flavin-bound Glucose Dehydrogenase (FGDH)
1-1. Glucose Dehydrogenase Activity A glucose dehydrogenase (GDH) is an enzyme that has a physicochemical property of catalyzing a reaction in which hydroxy groups of glucose are oxidized to produce glucono-δ-lactone in the presence of an electron acceptor. In this specification, this physicochemical property represents glucose dehydrogenase activity, and the terms "enzyme activity" and "activity" represent this enzyme activity unless otherwise noted. The electron acceptor is not limited as long as it can accept electrons in a reaction catalyzed by GDH. For example, 2,6-dichlorophenolindophenol (DCPIP), phenazine methosulfate (PMS), 1-methoxy-5-methylphenazium methylsulfate, and ferricyanide compounds may be used.

Various methods are known for measuring glucose dehydrogenase activity. A method used in this specification is a method using DCPIP as an electron acceptor and measuring the activity based on the change in absorbance of a sample at a wavelength of 600 nm before and after the reaction. The following are the specific reagent composition and measurement conditions unless otherwise noted.

Method for Measuring Glucose Dehydrogenase Activity
Reagent
150 mM phosphate buffer solution containing 0.6 M D-glucose, pH of 6.5 (containing 0.1% Triton X-100)
1.64 mM 2,6-dichlorophenolindophenol (DCPIP) solution The reaction reagent is obtained by mixing 20 mL of the phosphate buffer solution containing D-glucose and 10 mL of the DCPIP solution.
Measurement Conditions The reaction reagent (3 mL) is preheated at 37° C. for 5 minutes. A GDH solution (0.1 mL) is added and gently mixed. Water is used as a control, and changes in absorbance at 600 nm are recorded for 5 minutes by using a spectrophotometer at a controlled temperature of 37° C. Based on the linear portion (i.e., after the reaction rate becomes constant), the change in absorbance per minute ($\Delta OD_{TEST}$) is measured. In a blind test, a solvent used for dissolving GDH is added to the reagent mixture in place of the GDH solution, and the change in absorbance per minute ($\Delta OD_{BLANK}$) is measured in a similar manner. Based on the obtained values, the GDH activity is determined by the following equation. Here, one unit (U) of the GDH activity is equal to the enzyme amount that reduces 1 μmol of DCPIP in 1 minute in the presence of D-glucose at a concentration of 1 M.

$$\text{Activity (U/mL)} = \{-(\Delta OD_{TEST} - \Delta OD_{BLANK}) \times 3.1 \times \text{dilution factor}\} / \{16.3 \times 0.1 \times 1.0\}$$

In the equation, 3.1 is the total liquid amount (mL) of the reaction reagent and the enzyme solution, 16.3 is the millimolar extinction coefficient ($cm^2/\mu mol$) under conditions in which the activity is measured, 0.1 is the amount (mL) of the enzyme solution, and 1.0 is the optical path length (cm) of the cell. In this specification, the enzyme activity is measured according to this measurement method unless otherwise indicated.

The GDH of the present invention refers to flavin-bound GDH (FGDH), which requires flavin as a prosthetic group.

The FGDH of the present invention is preferably isolated FGDH or purified FGDH. The FGDH of the present invention may be in a state of being dissolved in a solution described above that is suitable for storage or in a freeze-dried state (e.g., powder). The expression "isolated" used in regard to the enzyme (FGDH) of the present invention refers to a state in which the enzyme is substantially free of components (e.g., host-cell-derived contaminating proteins, other components, and culture solution) other than the enzyme. Specifically, for example, the isolated enzyme of the present invention contains contaminating proteins in an amount of less than about 20%, preferably less than about 10%, more preferably less than about 5%, even more preferably less than about 1%, of the total (by weight). It is also possible for the FGDH of the present invention to be present in a solution (e.g., buffer) suitable for storage or for measurement of enzyme activity.

1-2. Substrate Specificity

The FGDH of the present invention has excellent substrate specificity. In particular, the FGDH of the present invention has significantly reduced reactivity at least to D-xylose, compared to the reactivity to D-glucose. More specifically, the FGDH of the present invention has reactivity to D-xylose of preferably 2% or less, more preferably 1.0% or less, still more preferably 0.7% or less, even more preferably 0.5% or less, and still even more preferably 0.2% or less, based on the reactivity to D-glucose at the same concentration taken as 100%.

In addition to the low reactivity to D-xylose, it is preferable that the FGDH of the present invention also have low reactivity to D-galactose and maltose. The FGDH of the present invention has reactivity to D-galactose of preferably 2% or less, more preferably 1.0% or less, still more preferably 0.7% or less, even more preferably 0.5% or less, and still even more preferably 0.2% or less, based on the reactivity to D-glucose at the same concentration taken as 100%.

The FGDH of the present invention has reactivity to maltose of preferably 2% or less, more preferably 1.0% or less, still more preferably 0.7% or less, and even more preferably 0.6% or less, based on the reactivity to D-glucose at the same concentration taken as 100%.

In this specification, the reactivity of FGDH of the present invention to each sugar can be measured by replacing D-glucose with another sugar (e.g., D-xylose, D-galactose, or maltose) in a method for measuring the glucose dehydrogenase activity described in Section 1-1 above, and comparing the obtained activity with that obtained with respect to D-glucose. For comparison, the concentration of each sugar is 50 mM. Further, the substrate specificity is measured at a final enzyme concentration of the reaction liquid of 3.3 μg/mL when the reactivity to glucose is measured, and of 1.4 mg/mL when the reactivity to xylose, maltose, or galactose is measured.

The FGDH of the present invention having such excellent substrate specificity is preferably used as an enzyme for accurately measuring the amount of glucose in a sample. Specifically, it is possible for the FGDH of the present invention to accurately measure the amount of target D-glucose even when the sample contains impurities, such as maltose, D-galactose, and D-xylose. Therefore, this enzyme of the present invention is considered to be suitable for applications where impurities in a sample are a concern or expected (typically, suitable for measuring the amount of glucose in blood). In addition to these applications, this enzyme is also applicable to various applications and is highly versatile.

1-3. Optimal Activity PH

The FGDH of the present invention preferably has the highest activity at a pH of 6.3 (phosphate buffer solution), as shown in the Examples below. Further, at a pH of 5.5 to 6.5 (MES-NaOH buffer solution) and a pH of 6.3 to 7.7 (phosphate buffer solution), the FGDH of the present invention has a relative activity of preferably 80% or more, based on the activity at a pH of 6.3 (phosphate buffer solution) taken as 100%. Specifically, the FGDH of the present invention has an optimal activity pH of 6.3 to 6.7, and preferably 6.3.

1-4. Optimal Activity Temperature

The FGDH of the present invention has an optimal activity temperature of preferably 34 to 47° C. The optimal activity temperature of 34 to 47° C. as used herein typically means that the temperature is more or less within a range of 34 to 47° C., and the range further includes an acceptable allowance to some extent. In this specification, the optimal activity temperature can be calculated by measuring the enzyme activity in a potassium phosphate buffer solution (pH of 7.0) at a final enzyme concentration of the reaction liquid (3.3 μg/mL), as shown in the Examples below.

1-5. pH Stability

In this specification, when 2 U/mL of enzyme that has been treated at 25° C. for 16 hours under specific pH conditions has remaining enzyme activity of 80% or more compared to the enzyme activity of the same enzyme before treatment, this enzyme is considered to be stable under these pH conditions. The FGDH of the present invention is preferably stable at least within the entire pH range of 4.5 to 7.5.

1-6. Temperature Stability

In this specification, when 10 U/mL of enzyme that has been treated for 15 minutes in an appropriate buffer solution (e.g., potassium acetate buffer (pH of 5.0)) under specific temperature conditions has remaining enzyme activity of 80% or more compared to the enzyme activity of the same enzyme before treatment, this enzyme is considered to be stable under these temperature conditions. The FGDH of the present invention is preferably stable at least at 45° C. or less (i.e., within a temperature range of 0 to 45° C.)

The FGDH of the present invention preferably has at least one or more, more preferably 2 or more, still more preferably 3 or more, even more preferably 4 or more, and further preferably all, of the characteristics described in Sections 1-2 to 1-6 above. The FGDH of the present invention may have any combination of the characteristics described in Sections 1-2 to 1-6 above. It is preferable that the FGDH of the present invention has the characteristic described in Section 1-2, and further has at least one characteristic selected from the group consisting of the characteristics described in Sections 1-3, 1-4, 1-5, and 1-6.

1-7. Molecular Weight

The polypeptide moiety constituting the FGDH of the present invention has a molecular weight of about 70 kDa as measured by SDS-PAGE. "About 70 kDa" includes a range in which a person skilled in the art would usually determine that the band is present at a position of 70 kDa when the molecular weight is measured by SDS-PAGE. "Polypeptide moiety" refers to FGDH substantially not having an attached sugar chain. When the FGDH of the present invention produced by microorganisms is in a glycosylated form, heat treatment or glycohydrolase treatment may be performed so that the sugar chains are removed (i.e., so that the polypeptide moiety is obtained). The state of substantially not having an attached sugar chain allows the existence of sugar chains necessarily remaining after heat treatment or glycohydrolase treatment of the FGDH in a glycosylated form. Therefore, when FGDH is originally not in a glycosylated form, the FGDH itself corresponds to the polypeptide moiety.

Various methods are known for removing sugar chains from FGDH in a glycosylated form. This specification uses a method comprising denaturing the FGDH in a glycosylated form by heat treatment at 100° C. for 10 minutes, followed by treatment at 37° C. for 6 hours with N-glycosidase Endo H (produced by New England Biolabs), as shown in the Examples below.

When the FGDH of the present invention has an attached sugar chain, its molecular weight is not limited as long as there is no adverse effect on the glucose dehydrogenase activity, substrate specificity, specific activity, and the like. For example, when the FGDH of the present invention has an attached sugar chain, the molecular weight is preferably 80 to 100 kDa as measured by SDS-PAGE. Considering that it better stabilizes the enzyme, and enhances water solubility to be easily dissolved in water, FGDH in a glycosylated form is preferable.

The molecular weight measurement by SDS-PAGE may be performed using general techniques and devices with the use of commercially available molecular weight markers.

1-8. Origin

The origin of the FGDH of the present invention is not particularly limited as long as the FGDH has the characteristics described above. The FGDH of the invention can be derived from, for example, microorganisms belonging to the genus *Arthrinium* and the genus *Apiospora*, which is the sexual stage of *Arthrinium*. The microorganisms belonging to the genus *Arthrinium* are not particularly limited. Examples include *Arthrinium japonicum, Arthrinium phaeospermum, Arthrinium terminalis, Arthrinium saccharicola, Arthrinium sacchari, Arthrinium serenense, Arthrinium arundinis, Arthrinium euphaubie, Arthrinium* RD000305, RD000313, RD000319, RD000334, RD000345, RD000346, RD000347, RD000351, RD000431, RD000454, RD000463, RD001987, RD006060, RD056943, RD056964, RD058144, RD059544, RD060455, and RD060458. The microorganisms belonging to the genus *Apiospora* are not particularly limited. Examples include *Apiospora montagnei, Apiospora setosa, Apiospora tintinnabula*, and the like. More specific examples include *Arthrinium sacchari. Arthrinium sacchari* was deposited in the National Institute of Technology and Evaluation, Patent Microorganisms Depositary (Kazusa Kamatari 2-5-8, Kisarazu, Chiba, 292-0818, Japan), was accepted on Aug. 22, 2012 under Accession No. NITE ABP-1408, and can be obtained after completing predetermined procedures.

Examples of other organisms from which the FGDH of the present invention is derived include microorganisms living in soil, rivers, lakes, and other water systems; microorganisms living in oceans; microorganisms indigenously present in the surface of or inside various animals or plants, and the like. As an isolation source, it is also possible to use microorganisms that thrive in low-temperature environments; high-temperature environments such as volcanoes; anoxic, high-pressure, and aphotic environments such as deep seas; and special environments such as oil fields.

In addition to FGDH directly isolated from microorganisms, the FGDH of the present invention also includes FGDH obtained through protein engineering methods by which the amino acid sequence, etc., of isolated FGDH has been modified, and FGDH obtained through genetic engineering techniques by which the isolated FGDH has been modified. For example, it is possible to use enzymes that are isolated from, for example, the above microorganisms of the genus *Arthrinium* and the genus *Apiospora*, which is the sexual stage of *Arthrinium*, and that are modified to have the characteristics described above. More specifically, it is also possible to use an enzyme that is derived from the microorganisms belonging to *Arthrinium sacchari* and that is modified.

2. Method for Producing Flavin-Bound Glucose Dehydrogenase

The FGDH of the present invention is produced by culturing microorganisms that are capable of producing the FGDH of the present invention. Microorganisms to be cultured are not particularly limited as long as they are capable of producing the FGDH of the present invention. For example, wild-type microorganisms belonging to the genus *Arthrinium* mentioned in Section 1 above are preferably used.

The culture method and culture conditions are not limited as long as the FGDH of the present invention is produced. Specifically as long as FGDH is produced, any method and conditions can be used that are suitable for the growth of the microorganisms to be used. Examples of culture conditions, such as the culture medium, culture temperature, and culture period, are described below.

There is no limitation on culture media as long as the microorganisms to be used can grow. Examples include those containing carbon sources, such as glucose, sucrose, gentiobiose, soluble starch, glycerin, dextrin, molasses, and organic acids; nitrogen sources, such as ammonium sulfate, ammonium carbonate, ammonium phosphate, ammonium acetate, peptone, yeast extract, corn steep liquor, casein hydrolysate, wheat bran, and meat extract; and inorganic salts, such as potassium salts, magnesium salts, sodium salts, phosphoric salts, manganese salts, iron salts, and zinc salts. To promote the growth of the microorganisms, it is also possible to add vitamins, amino acids, etc., to the medium.

When the FGDH of the present invention is obtained by culturing the microorganisms of the genus *Arthrinium*, the culture conditions may be selected in consideration of the nutritional and physiological properties of the microorganisms. Liquid culturing is performed in many cases. Industrially, aeration-agitation culturing is advantageous. In terms of productivity, however, solid culturing can be more advantageous.

The medium has a pH of, for example, about 3 to 8, and preferably about 5 to 7 as long as it is suitable for the growth of the microorganisms to be cultured. Culturing is performed at a culture temperature of usually about 10 to 50° C., preferably about 25 to 35° C., for 1 to 15 days, preferably about 3 to 7 days, under aerobic conditions. As a culture method, for example, shake culturing or aerobic submerged culturing using a jar fermenter may be used.

It is preferable for the FGDH to be collected from the culture solution or cells after culturing under the above conditions. When microorganisms that secrete FGDH out of the cells are used, the enzyme of the present invention can be obtained, for example, in the following manner. Specifically, the culture supernatant is filtered, centrifuged, etc., to remove insoluble matter, and separation and purification are then performed by suitably combining the following: ultrafiltration membrane concentration, ammonium sulfate precipitation and other forms of salting out, dialysis, various forms of chromatography, and the like. A flavin-bound glucose dehydrogenase produced by microorganisms that belong to the genus *Arthrinium* is basically a secretory protein.

In contrast, when the FGDH is collected from inside the cells, the enzyme of the present invention can be obtained, for example, in the following manner. Specifically, the cells are disrupted by pressure treatment, ultrasonic treatment, a mechanical technique, or techniques using enzymes such as lysozyme, and a surfactant and a chelating agent such as EDTA are optionally added to solubilize FGDH, which is then separated and collected as an aqueous solution, followed by separation and purification. It is also possible to perform this series of processes (cell disruption, separation, and purification) after collecting cells in advance from a culture solution by filtration, centrifugation, or the like.

Purification may be performed, for example, by suitably combining concentration such as vacuum concentration or membrane concentration; salting out with ammonium sulfate, sodium sulfate, or the like; fractional precipitation with a hydrophilic organic solvent such as methanol, ethanol, or acetone; heat treatment; isoelectric focusing; gel filtration with an adsorbent or a gel filtration agent; adsorption chromatography; ion-exchange chromatography; affinity chromatography; and the like.

When column chromatography is used, for example, a gel filtration using Sephadex gel (produced by GE Healthcare Bioscience) and chromatography using DEAE Sepharose CL-6B (produced by GE Healthcare Bioscience) or Octyl Sepharose CL-6B (produced by GE Healthcare Bioscience) may be used. It is preferable that the purified enzyme preparation be purified to the extent that the enzyme migrates as a single band on electrophoresis (SDS-PAGE).

In harvesting (e.g., extracting or purifying) a protein having glucose dehydrogenase activity from a culture solution, any of the following may be used, singly or in multiple, as indices: glucose dehydrogenase activity, action on maltose, thermal stability, and the like.

In each purification process, in principle, the GDH activity is used as an index for fractionation, thereby proceeding to the next step. This does not apply, however, if the appropriate conditions can be set in advance such as by performing a preliminary test.

To obtain the enzyme of the present invention as a recombinant protein, various modifications can be made. For example, DNA encoding the enzyme of the present invention and other appropriate DNA are inserted into the same vector, which is used to produce a recombinant protein. In this manner, the enzyme of the present invention made of a recombinant protein in which arbitrary peptides or proteins are linked together can be obtained. It is also possible to add sugar chains and/or lipid, or to make modifications that cause processing at the N-terminus or C-terminus. These modifications enable simplifying the extraction and purification of recombinant proteins, as well as the addition of biological functions, and the like.

The DNA encoding the enzyme of the present invention may be easily prepared by using standard genetic engineering techniques, molecular biological techniques, biochemical techniques, and the like (see, for example, Molecular Cloning, 3rd Ed., Cold Spring Harbor Lab. Press (2001)).

Standard genetic engineering techniques can be performed, specifically, by preparing a cDNA library from suitable source microorganisms that can express the FGDH of the present invention according to a known method, and selecting desired clones using probes or antibodies specific to the DNA sequence of the present invention (see, for example, Proc. Natl. Acad. Sci. USA., 78, 6613 (1981)). The source microorganisms for preparing a cDNA library are not limited as long as they express the FGDH of the present invention, but are preferably microorganisms of the genus *Arthrinium*. More specific examples include the microorganisms described above in Section 1-8.

An appropriate type of vector is selected in consideration of the type of host cell. Specific examples of vectors include plasmid vectors, cosmid vectors, phage vectors, viral vectors (e.g., adenoviral vectors, adeno-associated viral vectors, retroviral vectors, herpesviral vectors), and the like. Vectors suitably used when filamentous fungi are used as hosts may also be used. It is also possible to use vectors suitable for self-cloning.

In the use of *Escherichia coli* as a host, it is possible to use, for example, an M13 phage or modifications thereof, a λ phage or modifications thereof, pBR322 or modifications thereof (e.g., pB325, pAT153, pUC8), and the like. In the use of yeasts as hosts, pYepSec1, pMFa, pYES2, and the like, may be used. In the use of insect cells as hosts, for example, pAc and pVL may be used. In the use of mammalian cells as hosts, for example, pCDM8 and pMT2PC may be used. The vectors are not limited to these examples.

Insertion of the DNA of the present invention into a vector, insertion of a selection marker gene (if required), insertion of a promoter (if required), and the like, may be performed using standard recombinant DNA technology.

The means for introducing the DNA encoding the enzyme of the present invention into a host cell is not particularly limited. For example, the DNA contained in the vector mentioned above is introduced into a host cell. Host cells are not particularly limited as long as they can express the DNA of the present invention to produce FGDH. Specifically, it is possible to use prokaryotic cells, such as *Escherichia coli* and *Bacillus subtilis*; and eukaryotic cells, such as yeast, mold, insect cells, plant cultured cells, and mammal cells. Examples of prokaryotic cells used as a host include the genera *Escherichia, Bacillus, Brevibacillus, Corynebacterium*, and the like. Examples of the genera include *Escherichia coli* C600, *Escherichia coli* HB101, *Escherichia coli* DH5α, *Bacillus subtilis, Brevibacillus choshinensis, Corynebacterium glutamicum*, and the like. Examples of the vectors include pBR322, pUC19, pBluescript, and the like. Examples of yeasts used as a host include the genera *Saccharomyces, Schizosaccharomyces, Candida, Pichia, Cryptococcus*, and the like. Examples of the genera include *Saccharomyces cerevisiae, Schizosaccharomyces pombe, Candida utilis, Pichia pastoris, Cryptococcus* sp., and the like. Examples of the vectors include pAUR101, pAUR224, pYE32, and the like.

Examples of filamentous fungal cells used as a host include the genera *Aspergillus, Trichoderma, Colletotrichum*, and the like.

Examples of the genera include *Aspergillus oryzae, Aspergillus niger, Trichoderma ressei, Mucor hiemalis, Arthrinium sacchari*, and the like. As a host, it is also preferable in the present invention to use microorganisms that belong to the genus *Arthrinium* from which the FGDH is isolated. Specifically, although in transformants, foreign DNA is generally present in a host cell, a preferable embodiment also includes transformants obtained by a self-cloning in which microorganisms from which the DNA is derived are used as a host.

The transformant of the present invention is preferably obtained by transfection or transformation of the expression vector described above. The transformation may be transient or stable transformation. Transfection or transformation may be performed by using a calcium phosphate co-sedimentation method, an electroporation method, a lipofection method, a microinjection method, a Hanahan method, a lithium acetate method, a protoplast-polyethylene glycol method, or the like.

3. Application of the FGDH of the Present Invention

The FGDH of the present invention is applicable to various products. In this specification, the term "product" refers to a product that contains the FGDH of the present invention and that constitutes a part or the whole of one set for a user to accomplish some application.

The product of the present invention may be used in various applications without any limitation. Typical examples thereof include a method for measuring a glucose concentration by causing FGDH to act on glucose.

An embodiment of the present invention also provides a method for measuring a glucose concentration, the method comprising causing the above flavin-bound glucose dehydrogenase to act on glucose. Methods for measuring glucose using glucose dehydrogenase have already been established in this technical field. The amount or concentration of glucose in various samples can be measured using the FGDH of the present invention according to known methods. The mode for the measurement is not limited, as long as the FGDH of the present invention is used to measure the amount or concentration of glucose. For example, the measurement may be performed by causing the FGDH of the present invention to act on glucose in a sample, and spectrophotometrically measuring the structural change of the electron acceptor (e.g., DCPIP) associated with glucose dehydrogenation. More specifically, the measurement may be performed according to the method described in Section 1-1 above. According to the present invention, it is possible for the glucose concentration to be measured by adding the FGDH of the present invention to a sample, or by adding the FGDH of the present invention to a sample, followed by mixing. The sample containing glucose is not limited. Examples of the samples include blood, beverages, foods, and the like. The amount of enzyme added to a sample is not limited as long as it is possible to measure the amount or concentration of glucose.

The glucose concentration can be measured using a sensor described later, for example, in the following manner. A buffer solution is placed in a thermostatic cell, and the temperature is maintained constant. Potassium ferricyanide, phenazine methosulfate, or the like, may be used as a mediator. An electrode on which the FGDH of the present invention is immobilized is used as a working electrode. Further, a counter electrode (e.g., platinum electrode) and a reference electrode (e.g., Ag/AgCl electrode) are used. A constant voltage is applied across the carbon electrode. After the current becomes constant, a sample containing glucose is added, and the increase in current is measured. The glucose concentration in the sample can be calculated based on the calibration curve prepared from glucose solutions of standard concentration.

Examples of the Product of the Present Invention Include a Glucose Assay Kit.

An embodiment of the present invention also provides a glucose assay kit containing the flavin-bound glucose dehydrogenase described above.

The glucose assay kit of the present invention contains the FGDH of the present invention in an amount sufficient for at least one assay. In addition to the FGDH of the present invention, the kit typically contains a buffer solution and a mediator required for the assay, a glucose standard solution for preparing a calibration curve, and instructions for use. The FGDH of the present invention may be provided in various forms, such as a freeze-dried reagent or a solution in an appropriate storage solution.

Other Examples of the Product of the Present Invention Include a Glucose Sensor.

One embodiment of the present invention also provides a glucose sensor containing the flavin-bound glucose dehydrogenase described above.

The glucose sensor of the present invention can be produced by immobilizing the enzyme of the present invention on an electrode, such as a carbon electrode, a gold electrode, or a platinum electrode. Examples of methods for immobilization include a method using a crosslinking reagent, a method for encapsulating the FGDH in a polymer matrix, a method for covering the FGDH with a dialysis membrane, methods using a photo-crosslinkable polymer, a conductive polymer, and a redox polymer, and the like. Alternatively, the FGDH of the present invention may be immobilized in a polymer or immobilized adsorptively onto an electrode, together with an electron mediator, such as ferrocene or its derivatives. These methods may also be used in combination. Since the FGDH of the present invention has excellent thermal stability, immobilization may be performed at a relatively high temperature (e.g., 50° C. or 55° C.). Typically, the FGDH of the present invention is immobilized on a carbon electrode using glutaraldehyde, followed by treatment with an amine-containing reagent. In this manner, the glutaraldehyde can be blocked.

The present invention is more specifically described below by presenting Examples. The descriptions of the Examples below are not intended to limit the present invention in any aspects.

EXAMPLES

Example 1

Screening of Strain

Screening was performed to isolate the strain of the present invention from soil in the following manner. A soil sample diluted with water was plated on a DP medium (dextrin 2.0%, polypeptone 1.0%, $KH_2PO_4$ 1.0%, agarose 1.5%), and the colonies were isolated. The isolated colonies were added to a solid medium obtained by sterilizing a medium containing 2 g of wheat germ and 2 mL of 2% glucose solution in an autoclave at 120° C. for 20 minutes, and were statically cultured at 25° C. for 5 to 7 days. After the culturing, 1 mL of 50 mM potassium phosphate buffer solution (pH of 6.0) was added, and the cells were sufficiently suspended by vortex mixing. After a small amount of glass beads were added to the suspension, the cells were disrupted using a beads shocker (Yasui Kikai Corporation) at 3,000 rpm for 3 minutes, twice, followed by centrifugation at 4° C. for 5 minutes at 2,000×g. The resulting supernatant was used as a crude enzyme solution. The glucose dehydrogenase activity of the crude enzyme solution was measured by using the method described in Example 2, and strains having glucose dehydrogenase activity were selected.

Example 2

Confirmation of Glucose Dehydrogenase Activity

The activity of glucose dehydrogenase in the crude enzyme solution obtained in Example 1 was measured according to the glucose dehydrogenase activity measurement method shown in Section 1-1 above. Table 1 shows the results.

TABLE 1

| Strain | Activity (U/ml) |
| --- | --- |
| *Arthrinium* sp. | 0.19 |

As shown in Table 1, GDH activity was confirmed in the crude enzyme solution from *Arthrinium sacchari*.

Example 3

Purification of GDH from *Arthrinium Sacchari*

50 mL of YPD medium (0.5% yeast extract, 1% peptone, and 2% glucose) was placed in a 500-mL Sakaguchi flask and sterilized in an autoclave, thereby preparing a preculture medium. A loopful of *Arthrinium sacchari* reconstituted in advance in a DP plate medium was inoculated into the preculture medium and subjected to shaking culture at 25° C. for 7 days at 180 rpm, thereby obtaining a seed culture solution.

Next, 7.0 L of a production medium (yeast extract 4.0%, glycerol 4.0%, pH of 6.0) was placed in a 10-L jar fermenter and sterilized in an autoclave, thereby obtaining a main culture medium. Then, 50 mL of the seed culture solution was inoculated into the main culture medium and was cultured for 7 days under the following conditions: culture temperature=25° C., stirring speed=350 rpm, air flow rate=2.0 L/min, and tube internal pressure=0.2 MPa. Thereafter, the culture solution was filtered, and the filtrate was concentrated using a UF membrane (Millipore) having a molecular weight cutoff of 8,000, and a 50-mM phosphate buffer solution (pH of 6.0) was added to the concentrated solution. This step was repeated to remove low-molecular substances.

Subsequently, ammonium sulfate was gradually added to the desalinated solution to give 0.3 saturation, and the resulting liquid was subjected to linear gradient elution with a 50-mM phosphate buffer solution (pH of 6.0) by being passed through a 500-mL PS Sepharose Fast Flow column (GE Healthcare) equilibrated in advance with a 50-mM potassium phosphate buffer solution (pH of 6.0) containing 0.3-saturated ammonium sulfate. Thereafter, the eluted GDH fraction was concentrated using a hollow fiber membrane (Spectrum Laboratories, Inc.) having a molecular weight cutoff of 10,000, and was passed through a DEAE Sepharose Fast Flow column (GE Healthcare) equilibrated with a 50-mM potassium phosphate buffer solution (pH of 6.0) to adsorb only contaminating proteins. The resulting liquid was then subjected to linear gradient elution with a 0-mM phosphate buffer solution (pH of 6.0) by being passed through a 50-mL Resource-Phe column (GE Healthcare) equilibrated with a 50-mM potassium phosphate buffer solution (pH of 6.0) containing 0.3-saturated ammonium sulfate. The eluted product was further passed through a Superdex S-200 column (GE Healthcare), thereby obtaining a purified enzyme (this GDH is hereinafter also referred to as "AsGDH"). The AsGDH was denatured by heating at 100° C. for 10 minutes, and then treated at 37° C. for an hour with 5 U of Endo H (New England Biolabs Inc.), thereby decomposing the sugar chain added to the protein. Thereafter, the obtained purified enzyme was subjected to SDS-PAGE (Phast Gel (10-15%) PhastSystem, GE Healthcare) to determine the molecular weight; the AsGDH had a molecular weight of about 70,000 Da. Similarly, the AsGDH that was not subjected to sugar-chain degradation was subjected to SDS-PAGE to determine the molecular weight to be about 80 to 100 kDa.

Example 4 Substrate Specificity

In accordance with the GDH activity measurement method described in Section 1-1 above, the activity of the AsGDH purified in Example 4 was measured with respect to D-glucose, maltose, D-galactose, and D-xylose as substrates. The activity with respect to other sugars was determined based on the activity with respect to D-glucose as a substrate taken as 100%. The concentration of each sugar was 50 mM. Table 2 shows the results. The reaction was performed at a final enzyme concentration of 3.3 µg/mL for glucose, and 1.4 mg/mL for other sugars. The following enzyme activity measurement conditions were used in the present Example. 1.79 mL of a 100-mM phosphate buffer solution (pH of 7.0), 0.08 mL of a 1.25M D-glucose solution, and 0.01 mL of a 20-mM DCPIP solution were mixed, and the mixture was kept warm at a temperature of 37° C. for 5 minutes. Then, 0.02 mL of a 20-mM PMS solution and 0.1 mL of an enzyme sample solution were added to start the reaction. The absorbency at the beginning of the reaction and the absorbency over time were measured, and the decrement amount ($\Delta A600$) of the absorbency per minute at 600 nm with the advance of the enzyme reaction was found, thereby calculating the activity of flavin-bound GDH according to the equation below. One U of the activity of the flavin-bound GDH is defined as equal to the enzyme amount that reduces 1 µmol of DCPIP in 1 minute at 37° C. in the presence of D-glucose having a concentration of 50 mM.

Activity (U/mL)={-($\Delta OD_{TEST}-\Delta OD_{BLANK}$)×2.0× dilution factor}/{16.3×0.1×1.0}

In the equation, 2.0 is the total liquid amount (mL) of the reaction reagent and the enzyme reagent, and 16.3 is the millimolar extinction coefficient (cm$^2$/µmol) under conditions in which the activity is measured, 0.1 is the amount (mL) of enzyme solution, 1.0 is the optical path length (cm) of the cell, and $\Delta OD_{BLANK}$ is the decrement amount of the absorbency per minute at 600 nm when the reaction was started by adding a 10-mM acetic acid buffer solution instead of an enzyme sample solution.

TABLE 2

| Sugar | Relative activity (%) |
| --- | --- |
| D-Glucose | 100.0 |
| Maltose | 0.6% or less |
| D-Galactose | 0.2% or less |
| D-Xylose | 0.2% or less |

The results of Table 2 reveal that the apparent activity of the purified AsGDH with respect to maltose, D-galactose, and D-xylose was 0.6% or less, 0.2% or less, and 0.2% or less, respectively, based on its activity with respect to D-glucose taken as 100%. These results demonstrate that the AsGDH of the present invention has excellent substrate specificity.

Example 7

Optimal Activity pH

Figure 1:
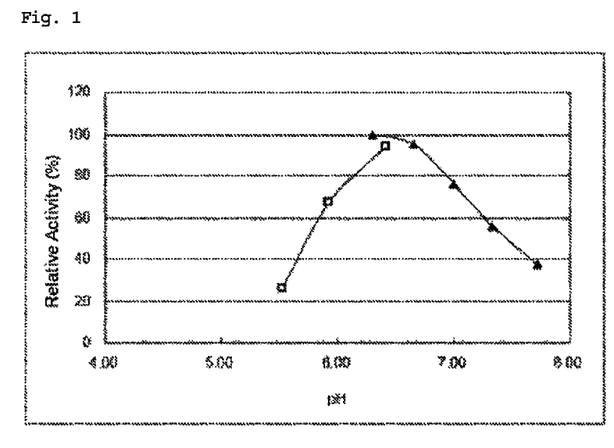
FIG. 1 is a graph showing the influence of pH on the activity of *Arthrinium sacchari*-derived GDH.

The optimal pH was found using the purified AsGDH enzyme liquid (0.5 U/mL) obtained in Example 4. An enzyme reaction was performed at 37° C. and different pH values using a 100-mM MES-NaOH buffer solution (pH of 5.5 to 6.5, plotted with white squares in FIG. 1), and a 100-mM potassium phosphate buffer solution (pH of 6.3 to 7.7, plotted with black triangles in FIG. 1) so as to compare the relative activity. FIG. 1 shows the results.

The results reveal that the optimal activity pH of the purified AsGDH was the highest at a pH of 6.3 when a potassium phosphate buffer solution was used. Further, the AsGDH showed a relative activity of 80% or more in a pH range of 6.3 to 6.7, based on the activity at a pH of 6.3 taken as 100%. These results demonstrate that the optimal activity pH of the purified AsGDH falls within a range of about 6.3 to 6.7.

Example 8

Optimal Activity Temperature

Figure 2:
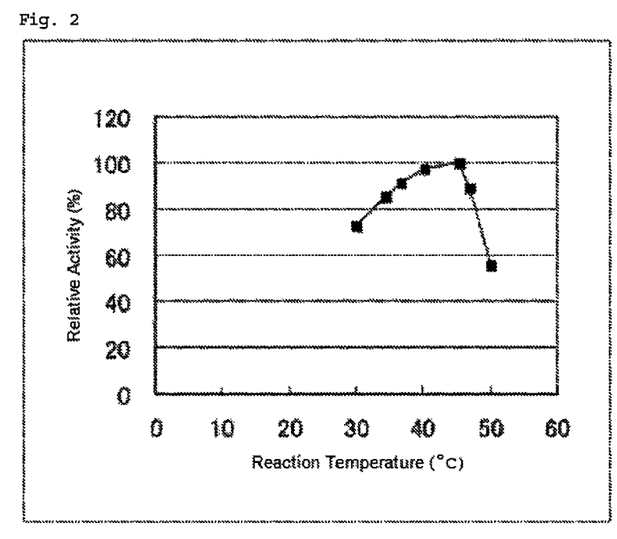
FIG. 2 is a graph showing the influence of temperature on the activity of *Arthrinium sacchari*-derived GDH.

The optimal activity temperature was found using the purified AsGDH enzyme liquid (3.5 µg/mL) obtained in Example 4. The activity at 30° C., 34° C., 37° C., 40° C., 45° C., 47° C., and 50° C. was measured. FIG. 2 shows the results. The present Example was measured under the same enzyme activity measurement conditions as in Example 4.

The results reveal that the activity value of the purified AsGDH was the highest at a temperature of 45° C., and the AsGDH showed a relative activity of 80% or more in a temperature range of 34° C. to 47° C., based on the highest activity. These results demonstrate that the optimal activity temperature of the purified AsGDH falls within a range of 34° C. to 47° C.

Example 9 pH Stability

Figure 3:
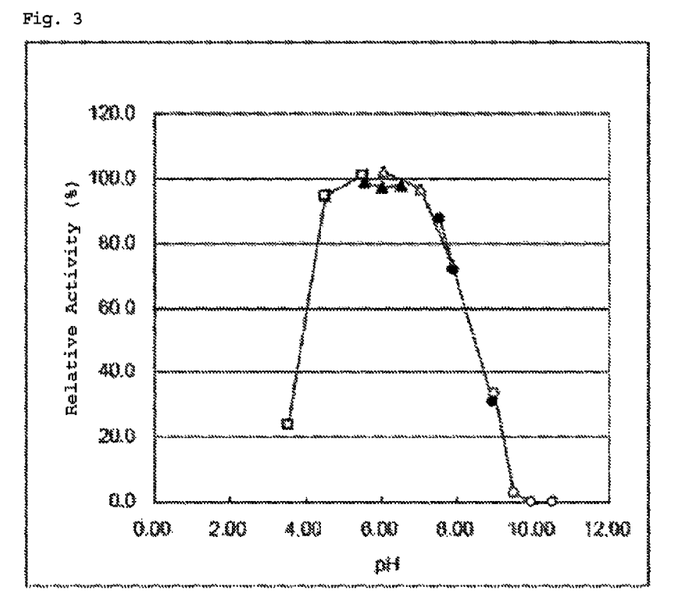
FIG. 3 is a graph showing the measurement results of the pH stability of *Arthrinium sacchari*-derived GDH.

The pH stability was measured using the AsGDH enzyme liquid (2 U/mL) obtained in Example 4. The activity with respect to glucose as the substrate was measured after the enzyme was retained for 16 hours at 25° C. in a 100-mM potassium acetate buffer solution (pH of 3.5 to 5.5, plotted with white squares in FIG. 3), a 100-mM MES-NaOH buffer solution (pH of 5.5 to 6.5, plotted with black triangles in FIG. 3), a 100-mM potassium phosphate buffer solution (pH of 6.0 to 8.0, plotted with white triangles in FIG. 3), a 100-mM Tris-HCl buffer solution (pH of 7.5 to 9.0, plotted with black circles in FIG. 3), or a 100-mM Glycine-NaOH buffer solution (pH of 9.0 to 10.5, plotted with white circles in FIG. 3). The activity before the treatment and the activity after the treatment were compared to find the remaining activity. FIG. 3 shows the results.

The results reveal that the purified AsGDH had remaining activity of 80% or more at a pH of 4.5 to 7.5. This demonstrates that the stable pH range of the purified AsGDH is 4.5 to 7.5.

Example 10

Temperature Stability

Figure 4:
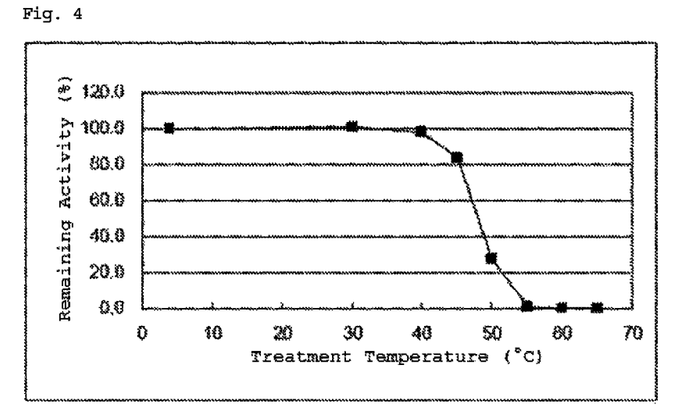
FIG. 4 is a graph showing the measurement results of the temperature stability of *Arthrinium sacchari*-derived GDH.

The temperature stability was measured using the purified AsGDH enzyme liquid (2 U/mL) obtained in Example 4. The AsGDH enzyme liquid was treated with 50 mM potassium phosphate buffer solution (pH of 6.0) for 15 minutes at different temperatures (4° C., 30° C., 40° C., 45° C., 50° C., 55° C., 60° C., and 65° C.) thereafter, the GDH activity before the treatment and the GDH activity after the treatment were compared to find the remaining activity. FIG. 4 shows the results.

The results reveal that the remaining activity of the purified AsGDH was 80% or more after the treatment at a temperature in a range of 4° C. to 45° C. This indicates that the stable temperature range of the purified AsGDH is 45° C. or less. Further, FIG. 4 shows that the remaining activity of the purified AsGDH was 90% or more after treatment at a temperature in a range of 4° C. to 40° C. This indicates that the purified AsGDH is significantly stable at a temperature of 40° C. or less.

Example 11

Measurement of Glucose Concentration Using Glucose Sensor

An electrode sensor in which a working electrode, a counter electrode, and a reference electrode were arranged on an insulating substrate was obtained from Bio Device Technology Co., Ltd. (Nomi, Ishikawa, Japan). In this electrode sensor, electrodes were printed on a substrate (4.0 mm×17 mm). 3 µL of an aqueous solution that is to serve as a reagent layer was dispensed onto the working electrode (about 1.3-mm$^2$ area) of this sensor. The aqueous solution that is to serve as a reagent layer had the following composition:

FAD-GDH
200 mM Potassium ferricyanide
50 mM Potassium phosphate buffer (pH of 7.0)

Figure 5:
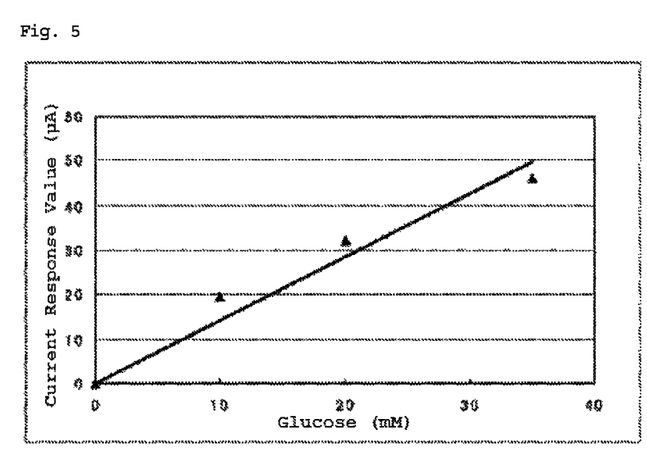
FIG. 5 is a graph showing the results of the glucose concentration measured with a glucose sensor produced using *Arthrinium sacchari*-derived GDH.

As FAD-GDH, the AsGDH purified in Example 3 was used. The resulting product was dried by heating at 35° C. for 15 minutes, thereby obtaining glucose sensor chips. Subsequently, glucose solutions having a concentration of 10 mM, 20 mM, or 35 mM were prepared. 15 µL each of these sample solutions was added dropwise with a micropipette to the above chip connected to a potentiostat. 35 seconds after the dropwise addition, a voltage of +300 mV was applied, and the electric current was measured. FIG. 5 shows the results of the current response value with respect to the glucose concentration.

The results reveal that the glucose sensor of the present invention showed a concentration-dependent increase in the current response value at least at a glucose concentration of 10 mM to 35 mM.

Example 12

Measurement of Glucose Concentration Using Glucose Sensor

Glucose sensor chips were produced in the same manner as in Example 11 by using 3 µL of an aqueous solution having the following composition and using the same electrode sensor as that used in Example 11.

AsGDH (purified in Example 3)
200 mM Potassium ferricyanide
50 mM Potassium phosphate buffer (pH 7.0)

The chips produced above were each connected to a potentiostat, and 15 µL of a glucose solution (concentration: 10 mM) was added dropwise with a micropipette onto the electrode. 35 seconds after the dropwise addition, a voltage of +300 mV was applied, and the electrical current was measured. Subsequently, a liquid containing glucose at a concentration of 10 mM as well as one kind of sugar selected from maltose, galactose, and xylose at a concentration of 20 mM was produced, and was reacted in the same manner as above. Table 3 shows the comparison results of the response signals between the case where a liquid containing only glucose was used and the case where a liquid containing glucose as well as other sugar was used. The values shown in Table 3 are expressed relative to the electrochemical signal intensity that was obtained when other sugar was not added and that is taken as 100.

TABLE 3

| Electrode added liquid | Relative Activity |
| --- | --- |
| 10 mM D-glucose alone | 100.0% |
| 10 mM D-glucose + 20 mM Maltose | 103.0% |
| 10 mM D-glucose + 20 mM D-Galactose | 96.8% |
| 10 mM D-glucose + 20 mM D-Xylose | 104.8% |

The results reveal that the sensor using AsGDH did not show a signal value increase attributable to the coexistence of maltose, galactose, or xylose.

The scope of the present invention is not limited to the above embodiments and Examples. The present invention also includes variations and modifications within the scope of the patent claims and within a range readily conceived of by those skilled in the art.

The entire content of papers, laid-open patent applications, and patent publications referred to in this specification is incorporated herein by reference.

INDUSTRIAL APPLICABILITY

The AsGDH of the present invention has excellent substrate specificity and enables more accurate measurement of the amount of glucose. Therefore, the AsGDH of the present invention is suitable, for example, for measuring blood glucose levels.

The invention claimed is:

1. An electrode comprising a flavin-bound glucose dehydrogenase having the following characteristics (1) to (6):
   (1) temperature stability: stable at a temperature of 45° C. or lower;
   (2) stable at a pH range of 4.5 to 7.5;
   (3) substrate specificity: the reactivity to D-xylose is 0.5% or less, based on the reactivity to D-glucose taken as 100%;
   (4) optimal activity temperature: 34 to 47° C.;
   (5) optimal activity pH: 6.3 to 6.7; and
   (6) a molecular weight of about 70 kDa when measured by SDS-PAGE;
   wherein the flavin-bound glucose dehydrogenase is immobilized onto the electrode.

2. The electrode according to claim 1, wherein the flavin-bound glucose dehydrogenase further has the following characteristic (7):
   (7) derived from microorganisms of the genus *Arthrinium* and the genus *Apiospora*, which is the sexual stage of *Arthrinium*.

3. The electrode according to claim 1, wherein the electrode is selected from the group consisting of a platinum electrode, a carbon electrode, and a gold electrode.

4. A glucose sensor comprising the electrode of claim 1.

5. A method of measuring glucose concentration in a sample comprising:
   (i) providing a solution comprising a flavin-bound glucose dehydrogenase having the following characteristics (1) to (6):
   (1) temperature stability: stable at a temperature of 45° C. or lower;
   (2) stable at a pH range of 4.5 to 7.5;
   (3) substrate specificity: the reactivity to D-xylose is 0.5% or less, based on the reactivity to D-glucose taken as 100%;
   (4) optimal activity temperature: 34 to 47° C.;
   (5) optimal activity pH: 6.3 to 6.7; and
   (6) a molecular weight of about 70 kDa when measured by SDS-PAGE;
   and a mediator,
   (ii) contacting the solution with the sample,
   (iii) measuring the transmission of an electron that is generated when the flavin-bound glucose dehydrogenase dehydrolzyes glucose in the sample, and
   (iv) correlating the measurement from step (iii) with a concentration of glucose in the sample.

6. The method according to claim 5, wherein the mediator is at least one selected from the group consisting of potassium ferricyanide and phenazine methosulfate.

7. The method according to claim 5, wherein the flavin-bound glucose dehydrogenase further has the following characteristic (7):
   (7) derived from microorganisms of the genus *Arthrinium* and the genus *Apiospora*, which is the sexual stage of *Arthrinium*.

8. The method according to claim 7, wherein the mediator is at least one selected from the group consisting of potassium ferricyanide and phenazine methosulfate.

* * * * *